United States Patent
Eskuri et al.

(10) Patent No.: US 7,857,826 B2
(45) Date of Patent: *Dec. 28, 2010

(54) CARTRIDGE EMBOLIC PROTECTION FILTER AND METHODS OF USE

(75) Inventors: Alan Eskuri, Hanover, MN (US); James G. Hansen, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1275 days.

This patent is subject to a terminal disclaimer.

(21) Appl. No.: 11/297,492

(22) Filed: Dec. 8, 2005

(65) Prior Publication Data

US 2006/0089665 A1 Apr. 27, 2006

Related U.S. Application Data

(63) Continuation of application No. 10/154,739, filed on May 23, 2002, now Pat. No. 7,001,406.

(51) Int. Cl.
*A61M 29/00* (2006.01)
(52) U.S. Cl. .................................................... 606/200
(58) Field of Classification Search ................ 606/200, 606/108, 198; 604/104–107; 623/1.11, 1.12
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,425,908 A | 1/1984 | Simon | |
| 4,643,184 A | 2/1987 | Mobin-Uddin | |
| 4,662,885 A | 5/1987 | DiPisa, Jr. | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,832,055 A * | 5/1989 | Palestrant ................... | 128/899 |
| 4,857,045 A | 8/1989 | Rydell | |
| 4,873,978 A | 10/1989 | Ginsburg | |
| 4,886,061 A | 12/1989 | Fischell et al. | |
| 4,969,891 A | 11/1990 | Gewertz | |
| 5,011,488 A | 4/1991 | Ginsburg | |
| 5,071,407 A | 12/1991 | Termin et al. | |
| 5,133,733 A | 7/1992 | Rasmussen et al. | |
| 5,160,342 A * | 11/1992 | Reger et al. .................. | 606/200 |

(Continued)

FOREIGN PATENT DOCUMENTS

WO 96/01591 A1 1/1996

*Primary Examiner*—Anhtuan T Nguyen
*Assistant Examiner*—Elizabeth Houston
(74) *Attorney, Agent, or Firm*—Seager, Tufte & Wickhem, LLC

(57) ABSTRACT

An embolic protection filter having a reduced profile for placement within a body lumen is disclosed. An embolic protection filter in accordance with the present invention includes a filter frame slidably and rotationally disposed along a guidewire, a plurality of retaining collars coupled to a proximal end of the filter frame, a plurality of expandable struts each having a proximal section adapted to slide within a corresponding retaining collar, and a filter mesh coupled to a distal section of the expandable struts for filtering embolic debris.

20 Claims, 1 Drawing Sheet

U.S. PATENT DOCUMENTS

| | | | |
|---|---|---|---|
| 5,192,286 A | 3/1993 | Phan et al. | |
| 5,324,304 A | 6/1994 | Rasmussen | |
| 5,329,942 A | 7/1994 | Gunther et al. | |
| 5,370,657 A | 12/1994 | Irie | |
| 5,415,630 A | 5/1995 | Gory et al. | |
| 5,419,774 A | 5/1995 | Willard et al. | |
| 5,462,529 A | 10/1995 | Simpson et al. | |
| 5,536,242 A | 7/1996 | Willard et al. | |
| 5,549,626 A | 8/1996 | Miller et al. | |
| 5,662,671 A | 9/1997 | Barbut et al. | |
| 5,669,933 A * | 9/1997 | Simon et al. | 600/200 |
| 5,769,816 A | 6/1998 | Barbut et al. | |
| 5,779,716 A | 7/1998 | Cano et al. | |
| 5,800,457 A | 9/1998 | Gelbfish | |
| 5,800,525 A | 9/1998 | Bachinski et al. | |
| 5,807,398 A | 9/1998 | Shaknovich | |
| 5,814,064 A | 9/1998 | Daniel et al. | |
| 5,833,650 A | 11/1998 | Imran | |
| 5,848,964 A | 12/1998 | Samuels | |
| 5,902,334 A | 5/1999 | Dwyer et al. | |
| 5,910,154 A | 6/1999 | Tsugita et al. | |
| 5,911,734 A | 6/1999 | Tsugita et al. | |
| 5,976,172 A * | 11/1999 | Homsma et al. | 606/200 |
| 6,039,744 A * | 3/2000 | Forber | 606/108 |
| 6,066,149 A | 5/2000 | Samson et al. | |
| 6,066,158 A | 5/2000 | Engelson et al. | |
| 6,129,739 A * | 10/2000 | Khosravi | 606/200 |
| 6,142,987 A | 11/2000 | Tsugita | |
| 6,152,946 A | 11/2000 | Broome et al. | |
| 6,168,579 B1 | 1/2001 | Tsugita | |
| 6,171,327 B1 * | 1/2001 | Daniel et al. | 606/200 |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,221,006 B1 | 4/2001 | Dubrul et al. | |
| 6,277,139 B1 | 8/2001 | Levinson et al. | |
| 6,325,815 B1 | 12/2001 | Kusleika et al. | |
| 6,371,971 B1 * | 4/2002 | Tsugita et al. | 606/200 |
| 6,537,295 B2 | 3/2003 | Petersen | |
| 6,540,722 B1 * | 4/2003 | Boyle et al. | 604/106 |
| 6,605,102 B1 | 8/2003 | Mazzocchi et al. | |
| 6,616,680 B1 * | 9/2003 | Thielen | 606/200 |
| 6,752,819 B1 | 6/2004 | Brady et al. | |
| 6,793,648 B2 | 9/2004 | Oslund et al. | |
| 6,793,666 B2 * | 9/2004 | Hansen et al. | 606/200 |
| 6,878,153 B2 | 4/2005 | Linder et al. | |
| 6,887,256 B2 | 5/2005 | Gilson et al. | |
| 6,918,921 B2 | 7/2005 | Brady et al. | |
| 6,951,570 B2 | 10/2005 | Linder et al. | |
| 6,964,672 B2 | 11/2005 | Brady et al. | |
| 6,974,469 B2 * | 12/2005 | Broome et al. | 606/200 |
| 6,991,642 B2 | 1/2006 | Petersen | |
| 6,997,939 B2 | 2/2006 | Linder et al. | |
| 7,014,647 B2 | 3/2006 | Brady et al. | |
| 2002/0095174 A1 | 7/2002 | Tsugita et al. | |
| 2002/0128678 A1 | 9/2002 | Petersen | |
| 2002/0183782 A1 | 12/2002 | Tsugita et al. | |
| 2003/0176887 A1 | 9/2003 | Petersen | |
| 2004/0073198 A1 | 4/2004 | Gilson et al. | |
| 2004/0260308 A1 | 12/2004 | Gilson et al. | |
| 2005/0288705 A1 | 12/2005 | Gilson et al. | |
| 2006/0004403 A1 | 1/2006 | Gilson et al. | |

* cited by examiner

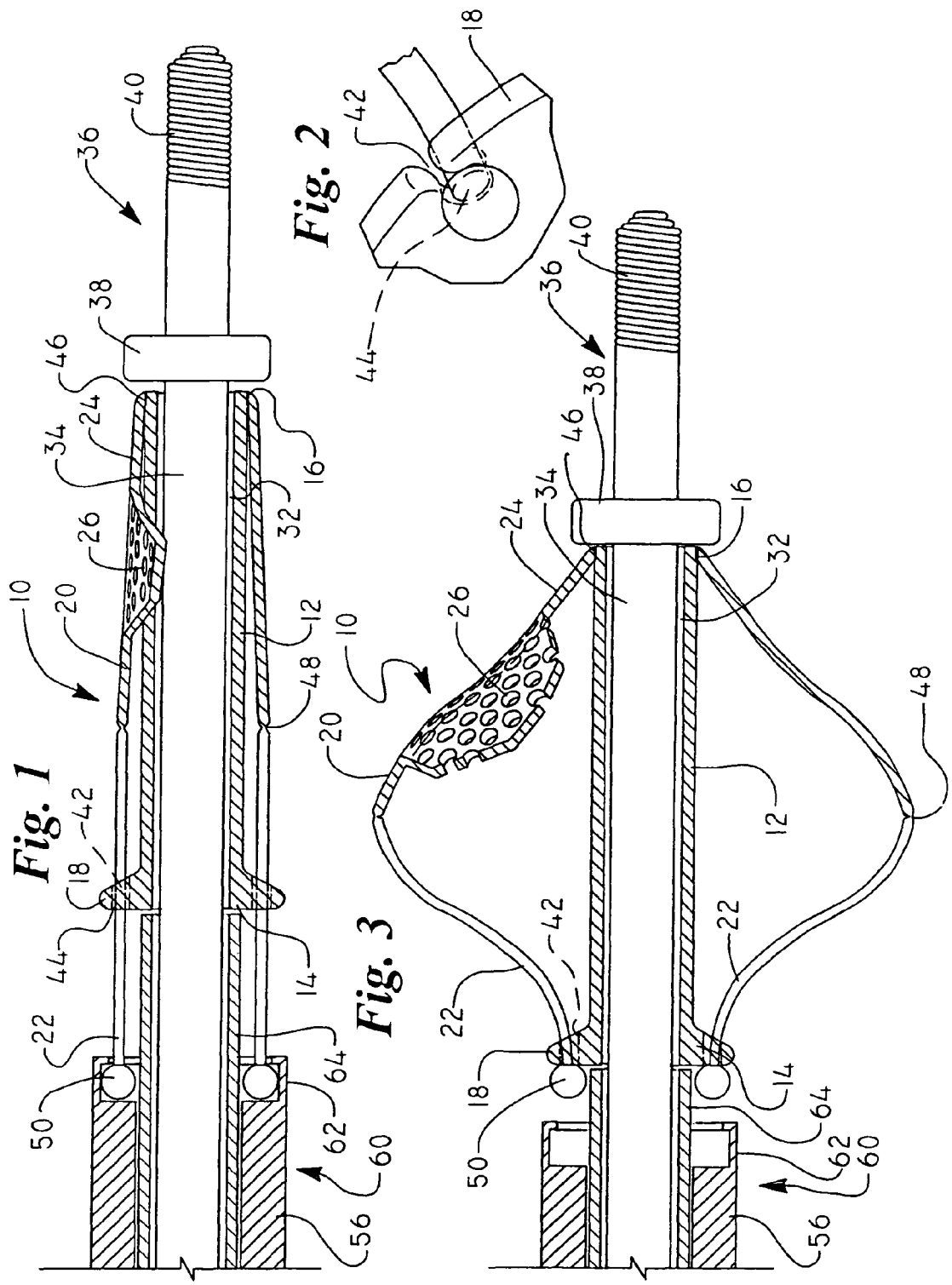

CARTRIDGE EMBOLIC PROTECTION FILTER AND METHODS OF USE

This is a continuation application of U.S. application Ser. No. 10/154,739 as filed on May 23, 2002 now U.S. Pat. No. 7,001,406.

FIELD OF THE INVENTION

The present invention relates generally to the field of embolic protection devices. More specifically, the present invention pertains to cartridge embolic protection filters having a reduced profile.

BACKGROUND OF THE INVENTION

Embolic protection filters are frequently used in conjunction with other therapeutic devices to filter embolic material such as plaque or thrombus from the blood stream. In a typical application such as percutaneous transluminal angioplasty (PTA) or percutaneous transluminal coronary angioplasty (PTCA), a collapsed filter is advanced along a guidewire to a location distal a lesion to be dilated. After the filter has been positioned and deployed within the vessel, an angioplasty catheter containing an angioplasty balloon is advanced along the guidewire and positioned proximal the lesion. The angioplasty balloon is then inflated, forcing the embolic material to become dislodged from the walls of the vessel and flow downstream, where it is collected by the filter. At the conclusion of the procedure, the guidewire, catheter, filter, and collected embolic debris are then removed from the body.

Catheters are frequently utilized in advancing and removing embolic protection filters within the body. These catheters often require relatively large chambers to transport the collapsed filter within the body, resulting in an enlarged profile. This enlarged profile may hinder placement of the device within the tortuous vasculature. In some cases, the delivery catheter may even aggravate the lesion to be dilated. As such, it is desireable to have an embolic protection filter with a compact profile to facilitate transport within the body.

SUMMARY OF THE INVENTION

The present invention relates generally to the field of embolic protection devices. More specifically, the present invention pertains to cartridge embolic protection filters having a reduced profile. In one embodiment of the present invention, an embolic protection filter comprises a filter frame slidably and rotationally disposed along a guidewire, a plurality of retaining collars coupled to the proximal end of the filter frame, a plurality of expandable struts each having a proximal portion adapted to slide within a corresponding retaining collar, and a filter mesh coupled to the expandable struts for filtering embolic debris. The expandable struts are biased to radially expand from a collapsed, radially compact position to an open, radially expanded position, when actuated.

To actuate the expandable struts between the collapsed (i.e. radially compact) position) and the open (i.e. radially expanded) position, an actuator mechanism is used. In one implementation of the present invention, an actuator mechanism comprises a tubular member having a channel on a distal end adapted to releasably lock onto a proximal section of the expandable struts. In another implementation of the present invention, an actuator mechanism comprises a tubular member having a threaded portion on a distal end adapted to engage a corresponding threaded surface disposed on a proximal section of the expandable struts.

In use, an advancing member is used to advance the actuator mechanism and collapsed filter along the guidewire distal a lesion. Once in place, the actuator mechanism is disengaged from the expandable struts, allowing the expandable struts to radially deploy within the vessel. To retrieve the embolic protection filter, the actuator mechanism is advanced distally along the guidewire until the distal end of the mechanism re-attaches to the expandable struts. Once attached, the operator retracts the actuator mechanism proximally, causing the expandable struts to radially collapse. The actuator, advancing member, and collapsed filter containing the collected embolic debris are then removed from the body.

BRIEF DESCRIPTION OF THE DRAWINGS

FIG. 1 is a cross-sectional view of an embolic protection filter in accordance with an embodiment of the present invention showing the filter in an closed, radially compact position;

FIG. 2 is a perspective view of the collar illustrated FIG. 1; and

FIG. 3 is a cross-sectional view of the embolic protection filter of FIG. 1, showing the filter in an open, radially expanded position.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, materials and manufacturing processes are illustrated for the various elements, those skilled in the art will recognize that many of the examples provided have suitable alternatives that may be utilized.

FIG. 1 is a cross-sectional view of an embolic protection filter 10 in accordance with an exemplary embodiment of the present invention. Embolic protection filter 10 includes a filter frame 12, a plurality of retaining collars 18, a plurality of expandable struts 20, and a filter mesh 26 attached to a distal section 24 of the expandable struts 20. The expandable struts 20, which are discussed in greater detail below, are biased to move between a collapsed, radially compact position, and an open, radially expanded position, when actuated.

Filter frame 12 defines a tubular member having a proximal end 14, a distal end 16, and a guidewire lumen 32. In a preferred application, filter frame 12 is slidably and rotationally disposable along a guidewire 34. Guidewire 34 has a proximal end (not shown), a distal end 36, and a distal stop 38 fixedly attached at or near distal end 36 thereof. Spring tip 40 can be placed on the distal end 36 of guidewire 34 to aid in navigating the guidewire 34 through the body.

Disposed about the proximal end 14 of filter frame 12 are a plurality of retaining collars 18. As shown in greater detail in FIG. 2, each of the retaining collars 18 defines a lumen 42 extending distally from an opening 44. In one implementation of the present invention, the retaining collars 18 and filter frame 12 are formed together from a single material (e.g. polypropylene or polyvinyl chloride) by a mold injection process. In an alternative implementation, the retaining collars 18 are attached to the proximal end 14 of filter frame 12 by crimping, soldering, bonding, or other suitable attachment means.

Coupled to the distal end 16 of filter frame 12 and extending proximally through lumen 42 of retaining collar 18 are expandable struts 20. Expandable struts 20 have a proximal section 22 and a distal section 24. The distal section 24 of expandable struts 20 is coupled to the distal end 16 of filter frame 12 at joint 46. The proximal section 22 of expandable struts 20, in turn, extends through lumen 42 of retaining collar 18 and terminates at a point proximate and proximal opening 44. In a preferred application, the proximal section 22 of expandable struts 20 is slidably disposed within lumen 42 formed by retaining collar 18.

Although the exemplary embodiment illustrated in FIG. 1 shows an embolic protection filter having two expandable struts 20 biased 180° apart from each other (as viewed from an end), any number of expandable struts may be employed. For example, an embolic protection filter in accordance with the present invention may include four expandable struts 20 circumferentially disposed 90° apart. In yet another example, an embolic protection filter in accordance with the present invention may include six expandable struts 20 circumferentially disposed 60° apart.

A pre-formed bend region 48 located along each of the expandable struts 20 between proximal sectional 22 and distal section 24 provides flexion between the sections 22, 24. Pre-formed bend region 48 biases each of the expandable struts 20 in an outward direction so that when unconstrained at the proximal end thereof, each of the expandable struts 20 radially expands towards the wall of the vessel. The bend region 48 may be offset along the length of each expandable strut 20 (if desired), or may be centrally located along the length each expandable strut 20.

The expandable struts 20 can be comprised of any number of suitable materials such as a 304 or 316 grade stainless steel, or polymeric materials such as polyvinylchloride (PVC) or polytetrafluoroethylene (PTFE). More preferably, the expandable struts 20 can be comprised of a shape-memory material such as nickel-titanium (NiTi) alloy. Nickel-titanium alloy exhibits pseudo-elastic capabilities at body temperature (37° C.), allowing it to endure a substantial amount of bending or flexing with relatively little residual strain. It is anticipated, however, that other biocompatible materials may be used.

A weld bead 50 disposed proximate the proximal section 22 of each expandable strut 20 prevents the proximal section 22 from detaching from the retaining collar 18. Weld bead 50 has an outer dimension that is greater than the inner diameter of lumen 42, thereby preventing distal movement of the weld bead beyond opening 44.

Attached to the distal section 24 of each expandable strut 20 is a filter mesh 26. Filter mesh 26 comprises a blood permeable sac furled about the distal section 24 of each expandable strut 20. In an open position, filter mesh 26 expands outwardly in the vessel, causing the dislodged embolic debris to collect within the sac.

To prevent the expandable struts 20 from expanding during transport of the embolic protection filter 10, an actuator mechanism 56 comprising a tubular member having a proximal end (not shown) and a distal end 60 can be used to actuate the expandable struts 20 between the collapsed, radially compact position and the open, radially expanded position. The distal end 60 of actuator mechanism 56 includes a channel 62, defined by a resilient portion of actuator mechanism 56, for temporarily locking the actuator mechanism 56 to each weld bead 50 to prevent the expandable struts 20 from deploying during transport.

Although channel 62 is shown in the exemplary embodiment of FIG. 1, it is to be recognized that other suitable locking mechanisms may be employed. For example, the proximal section 22 of each expandable strut 20 may include an enlarged outer diameter portion having a threaded surface adapted to engage a corresponding threaded surface disposed on the distal end 60 of actuator mechanism 56.

In the particular illustration of FIG. 1, embolic protection filter 10 is shown in the collapsed, radially compact position prior to deployment. The expandable struts 20 are constrained by applying a proximal force to actuator mechanism 56. The filter frame 12, in turn, is prevented from sliding proximally along the guidewire 34 by an advancing member 64 disposed proximal the proximal end 14 of filter frame 12. An optional hub (not shown) disposed about a proximal portion of the guidewire 34 can be utilized to prevent relative motion between the actuator mechanism 56 and the advancing member 64.

To actuate the embolic protection filter 10 within the vessel once placed distal a lesion, actuator mechanism 56 is retracted proximally while advancing member 64 is held stationary, causing the weld beads 50 to detach from the channel 62. When this occurs, the proximal section 22 of each expandable strut 20 slides distally through lumen 42 of retaining collar 18, causing each expandable strut 20 to radially expand towards the wall of the vessel, as shown in FIG. 3. As a result, filter mesh 26, which is furled about the distal section 24 of each expandable strut 20, is stretched across the diameter of the vessel to collect embolic debris dislodged during the procedure. After embolic protection filter 10 has been deployed, advancing member 64 can be retracted proximally along the guidewire 34 and removed from the body, or can be used to advance other intravascular devices along the guidewire 34.

Retrieval of the device from the body lumen subsequent to deployment is accomplished by reversing the aforesaid steps. To collapse the expandable struts 20, the operator slides the actuator mechanism 56 distally until weld balls 50 lock into channel 62. Once attached, the operator slides the actuator mechanism 56 proximally, causing the expandable struts 20 to collapse into the collapsed, radially compact position. Advancing member 64 can be used to prevent the embolic protection filter 10 from moving proximally during this process, if necessary.

Having thus described the several embodiments of the resent invention, those of skill in the art will readily appreciate that other embodiments may be made and used which fall within the scope of the claims attached hereto. Numerous advantages of the invention covered by this document have been set forth in the foregoing description. It will be understood, however, that this disclosure is, in many respects, only illustrative. Changes may be made in details, particular in matters of shape, size and arrangement of parts without exceeding the scope of the invention.

What is claimed is:

1. An embolic protection filter assembly, comprising:
  an elongate shaft having a distal end; a stop member disposed on the shaft adjacent the distal end;
  a filter frame coupled to the shaft, the filter frame having a tubular region disposed over the shaft, a proximal end region, a collar having a plurality of apertures therethrough adjacent the proximal end of the filter frame, and a strut region that defines one or more struts;
  wherein the one or more struts extend through and are slidable relative to the apertures of the collar; and
  a filter membrane coupled to the filter frame.

2. The filter assembly of claim 1, wherein each of the one or more struts has a flared end.

3. The filter assembly of claim 2, where flared ends of the one or more struts are defined by weld beads disposed on the one or more struts.

4. The filter assembly of claim 3, wherein the filter frame is configured to shift between a first collapsed configuration and a second expanded configuration.

5. The filter assembly of claim 4, wherein the flared ends of each of the one or more struts are seated against the collar when the filter frame is in the expanded configuration.

6. The filter assembly of claim 4, wherein the flared ends of each of the one or more struts are disposed a distance proximally from the collar when the filter frame is in the collapsed configuration.

7. The filter assembly of claim 4, further comprising an actuator member having a distal end with a channel formed therein, wherein the actuator member is adapted to shift the filter frame between the expanded configuration and the collapsed configuration.

8. The filter assembly of claim 7, wherein flared ends of the one or more struts are removably disposed in the channel.

9. The filter assembly of claim 7, wherein the actuator member further comprises an advancing member that is adapted to engage the tubular region of the filter frame.

10. A method for delivering an embolic protection filter, comprising the steps of:
providing a filter assembly, the filter assembly comprising:
an elongate shaft;
a filter frame coupled to the shaft, the filter frame having a proximal end region, a collar region having a plurality of apertures therethrough adjacent the proximal end region, a tubular region disposed over the shaft, and a strut region that defines one or more struts having flared ends,
wherein the one or more struts extend through and are slidable within and relative to the collar region, and
a filter membrane coupled to the filter frame;
providing an actuator member having a distal end with one or more channels formed therein;
engaging the actuator member with the flared ends of the one or more struts;
providing an advancing member;
engaging the advancing member with the tubular region of the filter frame;
proximally retracting the actuator member so that the one or more struts slide within and relative to the collar region and the flared ends become positioned a distance from the collar region; and
advancing the filter assembly through a body lumen to a target region.

11. The method of claim 10, wherein the step of engaging the actuator member with the flared ends of the one or more struts includes disposing the flared ends within the one or more channels.

12. The method of claim 10, wherein the step of proximally retracting the actuator member so that the one or more struts slide within the collar region and the flared ends become positioned a distance from the collar region includes collapsing the filter frame.

13. The method of claim 10, further comprising the step of disengaging the actuator member from the flared ends of the one or more struts.

14. The method of claim 13, wherein the one or more struts slide within the collar region so that the flared ends are seated against the collar region when the actuator member is disengaged from the flared ends.

15. An embolic protection filter assembly, comprising:
an elongate shaft;
a filter coupled to the shaft, the filter including a filter frame and a filter membrane coupled to the filter frame;
wherein the filter frame includes a tubular region disposed over the shaft, a proximal end, a collar having an aperture therethrough adjacent the proximal end of the filter frame, and a strut region that defines a strut;
wherein the strut extends through the aperture and is slidable relative to the aperture between a first position and a second position within the collar; and
wherein the filter is configured to shift between an expanded configuration when the strut is in the first position and a collapsed configuration when the strut is in the second position.

16. The filter assembly of claim 15, where the strut includes a flared end.

17. The filter assembly of claim 16, wherein the flared end of the strut is seated against the collar when the filter is in the expanded configuration.

18. The filter assembly of claim 17, wherein the flared end of the strut is positioned proximally of the collar when the filter is in the collapsed configuration.

19. The filter assembly of claim 15, further comprising an actuator member having a distal end with a channel formed therein, wherein the actuator member is adapted to shift the filter between the expanded configuration and the collapsed configuration.

20. The filter assembly of claim 19, further comprising an advancing member disposed adjacent the actuator member that is adapted to engage the tubular region of the filter frame.

* * * * *